US00PP36441P2

(12) United States Plant Patent
Bernuetz

(10) Patent No.: US PP36,441 P2
(45) Date of Patent: Feb. 11, 2025

(54) ***EUPHORBIA* PLANT NAMED 'BONPRI 1647'**

(50) Latin Name: ***Euphorbia pulcherrima* Willd. ex Klotzsch X *Euphorbia cornastra***
Varietal Denomination: BONPRI 1647

(71) Applicant: Andrew Bernuetz, Glenbrook (AU)

(72) Inventor: Andrew Bernuetz, Glenbrook (AU)

(73) Assignee: BONZA BONTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/621,009

(22) Filed: Mar. 28, 2024

(51) Int. Cl.
*A01H 5/02* (2018.01)
*A01H 6/38* (2018.01)

(52) U.S. Cl.
USPC ..... Plt./306

(58) Field of Classification Search
USPC ..... Plt./263.1, 302, 306
See application file for complete search history.

(56) References Cited

U.S. PATENT DOCUMENTS

PP30,367 P2 * 4/2019 Graff ..... A01H 6/385
Plt./303

* cited by examiner

*Primary Examiner* — Karen M Redden
(74) *Attorney, Agent, or Firm* — C. Anne Whealy

(57) ABSTRACT

A new and distinct cultivar of *Euphorbia* plant named 'BONPRI 1647', characterized by its upright and mounded plant habit; vigorous growth habit; freely branching habit; large inflorescences with bright purplish pink-colored flower bracts; and good post-production longevity.

2 Drawing Sheets

Figure 1:
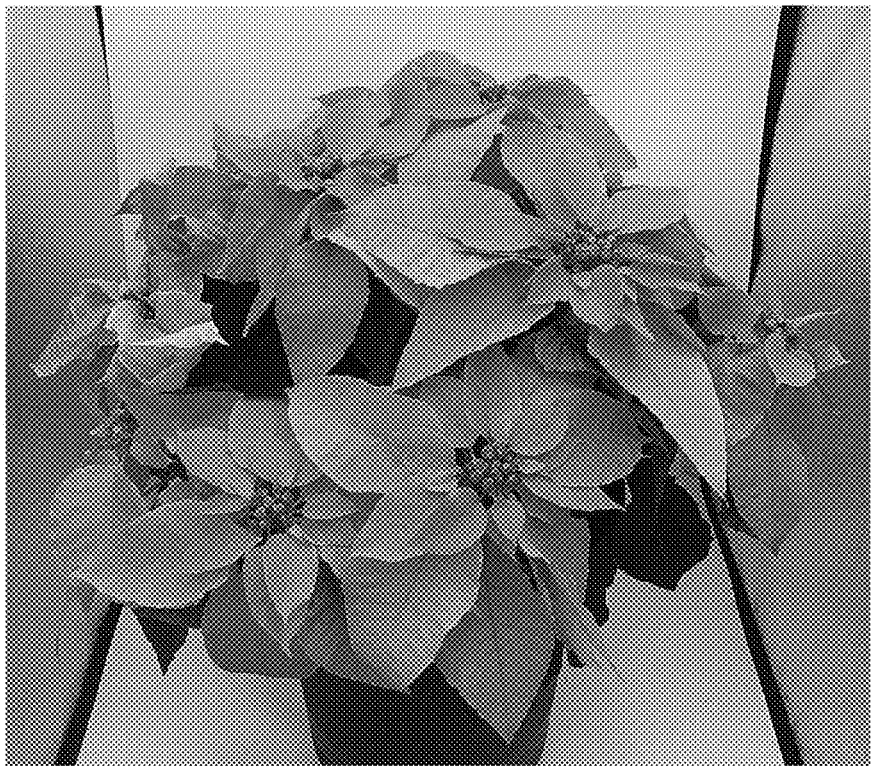

Botanical designation: *Euphorbia pulcherrima* Willd. ex Klotzsch X *Euphorbia cornastra.*
Cultivar denomination: 'BONPRI 1647'.

STATEMENT REGARDING PRIOR DISCLOSURES BY THE INVENTOR/APPLICANT & ASSIGNEE

The Inventor/Applicant and Assignee, Bonza Botanicals Pty., Ltd. of Yellow Rock, New South Wales, Australia, hereby confirm that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'BONPRI 1647'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number Eu14-95, not patented. The new *Euphorbia* plant was discovered and selected by the Inventor as a single flowering plant from within a population of plants of the mutation parent selection in a controlled greenhouse environment in Yellow Rock, New South Wales, Australia in October 2016.

Asexual reproduction of the new *Euphorbia* plant by terminal vegetative cuttings in a controlled greenhouse environment in Yellow Rock, New South Wales, Australia since October 2016 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'BONPRI 1647'. These characteristics in combination distinguish 'BONPRI 1647' as a new and distinct *Euphorbia* plant:

1. Upright and mounded plant habit.
2. Vigorous growth habit.
3. Freely branching habit.
4. Large inflorescences with bright purplish pink-colored flower bracts.
5. Good post-production longevity.

Plants of the new *Euphorbia* differ primarily from plants of the mutation parent selection in flower bract color as flower bracts of plants of the new *Euphorbia* are bright purplish pink in color whereas flower bracts of plants of the mutation parent selection are hot pink in color.

Plants of the new *Euphorbia* can be compared to plants of the *Euphorbia pulcherrima* Willd. ex Klotzsch X *Euphorbia cornastra* 'BONPRI 1095', disclosed in U.S. Plant Pat. No. 28,676. In side-by-side comparisons, plants of the new *Euphorbia* differ primarily from plants of 'BONPRI 1095' in the following characteristics:

1. Plants of the new *Euphorbia* are shorter and broader than plants of 'BONPRI 1095'.
2. Plants of the new *Euphorbia* are more freely branching than plants of 'BONPRI 1095'.
3. Plants of the new *Euphorbia* have fewer flower bracts per inflorescence than plants of 'BONPRI 1095'.
4. Plants of the new *Euphorbia* have smaller flower bracts per inflorescence than plants of 'BONPRI 1095'.
5. Plants of the new *Euphorbia* and 'BONPRI 1095' differ in flower bract color as flower bracts of plants of the new *Euphorbia* are bright purplish pink in color whereas flower bracts of plants of 'BONPRI 1095' are red purple in color with lighter red purple-colored margins.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet (FIG. 1) is a side perspective view of a typical flowering plant of 'BONPRI 1647' grown in a container.

Figure 2:
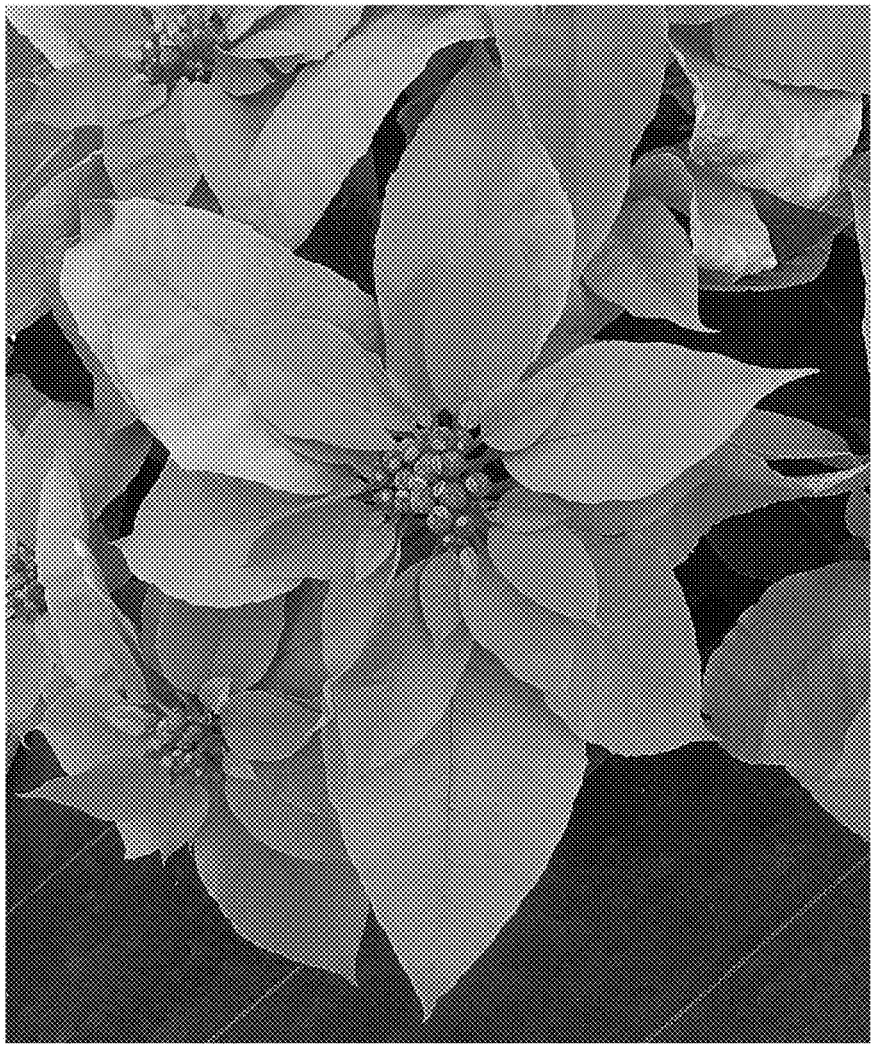

The photograph on the second sheet (FIG. 2) is a close-up view of a typical flowering plant of 'BONPRI 1647'.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'BONPRI 1647'.

Parentage: Naturally-occurring whole plant mutation of a proprietary selection of *Euphorbia pulcherrima* Willd. ex Klotzsch X *Euphorbia cornastra* identified as code number Eu14-95, not patented.

Propagation:

*Type*.—Terminal vegetative cuttings.

*Time to initiate roots, summer*.—About ten days at temperatures about 20° C. to 21° C.

*Time to initiate roots, winter*.—About twelve days at temperatures about 20° C. to 21° C.

*Time to produce a rooted young plant, summer*.—About 24 days at temperatures about 20° C. to 21° C.

*Time to produce a rooted young plant, winter*.—About 28 days at temperatures about 20° C. to 21° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 28 cm.

*Plant diameter or spread*.—About 42.5 cm.

*Lateral branch description*.—Branching habit: Freely branching habit, about seven to ten lateral branches develop per plant. Length: About 23.3 cm. Diameter: About 5.1 mm. Internode length: About 3 cm. Aspect: Mostly upright to slightly outwardly. Strength: Moderately strong. Texture: Smooth, glabrous. Color: Close to 144A.

*Leaf description*.—Arrangement: Alternate, simple. Length: About 9.8 cm. Width: About 6.2 cm. Shape: Lanceolate. Apex: Acute. Base: Rounded. Margin: Mostly entire, occasionally with few shallow lobes. Venation pattern: Pinnate, reticulate. Texture, upper and lower surfaces: Smooth, glabrous. Color: Developing and fully developed leaves, upper surface: Darker than 147A; venation, close to 138B. Developing and fully developed leaves, lower surface: Close to NN137B; venation, close to 138B. Petioles: Length: About 2.5 cm. Diameter: About 2.3 mm. Texture, upper and lower surfaces: Smooth, glabrous. Color, upper and lower surfaces: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about seven to ten inflorescences develop per plant.

*Inflorescence diameter*.—About 23.8 cm.

*Inflorescence height*.—About 6.9 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 50 to 56 days under natural season or photoinductive conditions in Japan.

*Post-production longevity*.—Good post-production longevity; plants of the new *Euphorbia* maintain good substance and bract color for about six to eight weeks.

*Flower bracts*.—Quantity per inflorescence: About 18. Length, largest bracts: About 10.9 cm. Width, largest bracts: About 5.9 cm. Aspect: Mostly horizontal and flat. Shape: Lanceolate. Apex: Acute. Base: Obtuse. Margin: Entire. Texture and luster, upper and lower surfaces: Smooth, glabrous; matte. Venation pattern:

Pinnate, reticulate. Color: Transitional bracts, upper surface: Random sectors, close to 137C and 62A. Transitional bracts, lower surface: Random sectors, close to 138D and 62D. Developing bracts, upper surface: Close to 58C. Developing bracts, lower surface: Close to 58D. Fully expanded bracts, upper surface: Close to 67D; venation, close to 67D; flower bracts resist fading with subsequent development. Fully expanded bracts, lower surface: Close to 68C; venation, close to 145D; flower bracts resist fading with subsequent development. Flower bract petioles: Length: About 1.7 cm. Diameter: About 2.3 mm. Texture, upper and lower surfaces: Smooth, glabrous. Color, upper and lower surfaces: Close to 144B tinged with close to 67D.

*Cyathia*.—Quantity per corymb: About 20. Diameter of cyathia cluster: About 2.9 cm. Height, individual cyathium: About 5.9 mm. Diameter, individual cyathium: About 5.3 mm. Shape, individual cyathium: Globose. Color: Distally, close to 58B, and proximally, close to 145A. Nectaries: Quantity per cyathium: About seven. Size: About 2.3 mm by 3.7 mm. Texture: Smooth, glabrous. Color: Close to 8B.

*Peduncles*.—Length: About 2.1 mm. Diameter: About 2.2 mm. Texture, upper and lower surfaces: Smooth, glabrous. Aspect: Mostly upright. Color, upper and lower surfaces: Close to 144B.

*Reproductive organs*.—To date, stamen and pistil development have not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'BONPRI 1647' as herein illustrated and described.

* * * * *